United States Patent [19]

Weinstein et al.

[11] Patent Number: 4,818,770

[45] Date of Patent: Apr. 4, 1989

[54] PREVENTION OF A PLANT DISEASE BY SPECIFIC INHIBITION OF FUNGAL POLYAMINE BIOSYNTHESIS

[75] Inventors: Leonard H. Weinstein; Arthur W. Galston, both of Ithaca, N.Y.

[73] Assignees: Boyce Thompson Institute For Plant Research, Ithaca, N.Y.; Yale University, New Haven, Conn.

[21] Appl. No.: 921,543

[22] Filed: Oct. 22, 1986

[51] Int. Cl.$^4$ .................... A01N 37/12; A01N 37/44
[52] U.S. Cl. .................................................. 514/564
[58] Field of Search .......................................... 514/564

[56] References Cited

U.S. PATENT DOCUMENTS 4,336,054 6/1982 Sjoerdsma .............................. 71/67
4,496,588 1/1985 Bey et al. ............................ 514/564

*Primary Examiner*—Allen J. Robinson
*Attorney, Agent, or Firm*—Ralph R. Barnard

[57] ABSTRACT

DL-alpha-Difluoromethylornithine (DFMO), an inhibitor of the polyamine biosynthetic enzyme ornithine decarboxylase (ODCase; EC 4.1.1.17), strongly retards the growth of several species of phytopathogenic fungi in vitro. Such inhibition can be completely reversed by putrescine or spermidine, confirming the essentiality of polyamines for growth of fungal hyphae. We now have discovered that DFMO can protect a range of plants against a wide range of fungi. For example, DFMO can protect bean plants (*Phaseolus vulgaris* Linnaeus cv. Pinto) against infection by uredospores of the bean rust fungus, *Uromyces phaseoli* Linnaeus, race O. Unifoliolate leaves of 10-day-old greenhouse-grown seedlings were sprayed with 400 ul per leaf of DFMO at various concentrations in 0.01% Tween 20 at pH 7.0 before or after inoculation with uredospores of Uromyces. After 16 hr in darkness in dew chambers to facilitate spore germination, plants were transferred to the greenhouse, arranged randomly, and examined for local lesions 7 days later. All concentrations of DFMO 0.50 mM or higher gave complete protection against the pathogen; at lower concentrations, postinoculation treatments with DFMO were generally more effective than preinoculation. The appearance of lesions on plants treated with lower concentration of DFMO was retarded 2-6 days. DFMO also confered protection on unsprayed parts of treated plants, indicating the translocation of some protective effect from sprayed areas. DL-alpha-Difluoromethylarginine, an analogous inhibitor of arginine decarboxylase (ADCase; EC 4.1.1.19), which is the rate-limiting enzyme in an alternative pathway for polyamine biosynthesis in higher plants, confers little protection even at 5mM. This emphasizes ornithine decarboxylase as the biochemical locus of choice for the prevention of plant diseases by inhibiting polyamine metabolism. DFMO has also been shown to be an effective synthetic fungicide for the following: protects tomato plants against Verticillium wilt fungus; protects wheat against stem rust fungus; protects wheat against powdery mildew fungus; protects Tendergreen bean plants against powdery mildew fungus; protects the MacIntosh apple leaf against the powdery mildew fungus; protects Ogle oats against leaf rust fungus; and protects corn against the corn rust fungus.

18 Claims, 3 Drawing Sheets

PREVENTION OF A PLANT DISEASE BY SPECIFIC INHIBITION OF FUNGAL POLYAMINE BIOSYNTHESIS

BACKGROUND OF THE INVENTION

This invention relates to the prevention of a plan disease by specific inhibition of fungal polyamine biosynthesis.

Fungi attack a wide variety of economically important crop plants, substantially reducing their quality and yield. The major weapon used against such phytopathogens has been synthetic fungicides. We report here on the fungicidal and plant protective efficacy of DL-alpha-difluorimethylornithine (DFMO), a specific inhibitor of ornithine decarboxylase (ODC; EC 4.1.1.17), the enzyme that provides fungi with the polyamines needed for normal growth and development (Tabor, C. W. & Tabor, H (1985) Microbiol. Rev. vol. 49, 81-99). The differential toxicity of DFMO for fungi and higher green plants depends on the fact that the latter have an alternative pathway, based on arginine decarboxylase (ADCl EC 4.1.1.19), for the synthesis of essential polyamines. In previous in vitro, experiments with fungi grown on synthetic media (Rajam, M. V. & Galston, A. W. (1985) Plant Cell Physiol. vol. 26, 683-692), we showed that DFMO is an effective inhibitor of mycelial growth and that such inhibitions are readily reversed by applied putrescine or spermidine. For the important rust and mildew diseases, however, the obligately and biotrophically parasitic organisms cannot always be grown on synthetic media. We accordingly undertook experiments which show that DFMO can inhibit germination, growth, and pathogenic effects of those fungi as well as non-obligate fungi, inoculated onto leaves of susceptible plants. In vitro experiments alone are inadequate to establish the efficacy of DFMO control of pathogenic fungi on plant hosts.

SUMMARY

This invention takes advantage of (a) the fact that ornithine decarboxylase is the principal enzyme of polyamine biosynthesis in fungi, (b) higher plants contain a second enzyme, arginine decarboxylase, in addition to ornithine decarboxylase to biosynthesize polyamines, and (c) DFMO is an irreversible inhibitor of ornithine decarboxylase. Therefore, it was discovered that fungal infection of higher plants could be diminished or arrested by applications of DFMO. By virtue of its dual pathways for polyamine biosynthesis, the higher plant was unaffected by such treatment, whereas the growth of pathogenic fungi on these plants was arrested by blockage of their sole pathway for polyamine biosynthesis.

When unifoliolate leaves of Pinto bean plants were inoculated with bean rust uredospores, application of 1 mM DFMO solutions made to some of the inoculated beans at intervals of one day for 5 days gave complete control of the disease for the first 3 days, after which the application of DFMO was less effective. (See Table 8) On this basis and considering the great sensitivity of the rust diseases in general to DFMO, there is no reason to believe that other rust infections would not respond in the same manner.

It does not appear necessary for DFMO solutions to cover the entire plant, because evidence is presented for protection of portions of plants that have not been sprayed. The protection conferred on unifoliolate leaves of bean plants inoculated with bean rust uredospores and sprayed with DFMO was found to persist and there was a translocation of the protective effect to another part of the plant.

While we have examined a number of plant parasitic fungus relationships where the teachings of the present invention apply, it should be noted that bean rust, wheat stem rust, wheat leaf rust, oat stem rust, corn rust, bean powdery mildew, apple powdery mildew, and wheat powdery mildew are obligate, or biotrophic, parasites. The effectiveness of DFMO to these groups of fungi lead one to conclude that there is every reason to believe that all rust diseases and most powdery mildew diseases would be controlled by application of DFMO. Although some non-obligate fungal parasites are effectively controlled by DFMO, others such as cucumber anthracnose, are not.

DFMO has been shown to control Verticillium wilt of tomato when applied to a portion of the plant remote from the point of infection by the pathogen. Thus, when the fungal spores were applied to the soil and DFMO was applied to the leaves, the wilt symptoms of the disease were greatly suppressed.

The discovery and teachings of the present invention are that DFMO will inhibit germination, growth and pathogenic effects of fungi on plants and will function as a fungicide when sprayed on the plants.

It is therefore a primary object of the present invention to provide a new and improved method of protecting plants against infecting fungi by applying DFMO to the plants.

It is still another object of the present invention to provide a new and improved method where pinto beans are given protection from infection by uredospores of the bean rust fungus by the application of DFMO.

It is another object of the present invention to provide a new and improved method where tomato plants are given protection from infection by Verticillium wilt fungus of the tomato by the application of DFMO.

It is another object of the present invention to provide a new and improved method where wheat is given protection from infection by leaf rust fungus.

It is still another object of the present invention to provide a new and improved method where wheat is given protection from infection by stem rust fungus by the application of DFMO.

It is still another object of the present invention to provide a new and improved method where wheat is given protection from infection by powdery mildew fungus by the application of DFMO.

It is still another object of the present invention to provide a new and improved method where Tendergreen bean plants are given protection from infection by powdery mildew fungus by the application of DFMO.

It is still another object of the present invention to provide a new and improved method where MacIntosh apple leaves are given protection from infection by powdery mildew fungus by the application of DFMO.

It is another object of the present invention to provide a new and improved method where Ogle oats are given protection from infection by stem rust fungus by the application of DFMO.

It is still another object of the present invention to provide a new and improved method where a plant or plants are given protection from infection by fungus by application of DFMO to a portion of each of the plants to be protected and the remaining parts of each plant, including new leaves thereof, are also protected.

It is an additional object of the present invention to provide a new and improved method where a plant or plants are given protection from infection by fungi by the application of DFMO to plant or a part thereof and each plant, including new leaves thereof, will be protected for a period of time determined by the concentration of the DFMO in a wetting agent.

It is another object of the present invention to provide a new use for a known chemical compound identified as DFMO wherein said compound is dissolved in a wetting agent and sprayed on a plant as a fungicide.

It is still another object of the present invention to provide a new and improved fungicide comprising a chemical compound known as DFMO dissolved in a wetting agent, said DFMO being useful for spraying plants to protect them from fungal pathogens which cause disease in that plant.

TEACHINGS OF THE PRESENT INVENTION APPLIED TO BEAN RUST

MATERIALS AND METHODS

It was discovered that DFMO can protect bean plants (Phaseolus vulgaris Linnaeus cv Pinto) against infection by uredospores of the bean rust fungus, Uromyces phaseoli Linnaeus, Race O. Pinto beams (Phaseolus vulgaris Linnaeus cv. Pinto) seeds were sown in a peat/vermiculite mix in 10-cm fiber pots. Four seeds were planted per pot and each pot was thinned to two uniform seedlings after emergence. The plants were then grown in a greenhouse supplied with air filtered through charcoal and Purafil II (Purafil, Atlanta) at 23°-25° C. ambient temperature, 70% relative humidity, and a 16-hour photoperiod.

Unifoliolate leaves of 10-day-old bean seedlings were sprayed (400 ul per leaf) with DFMO or alpha-difluoromethylarginine (DFMA) at concentrations of 0.01-5 mM, before or after inoculation with uredospores of the bean rust, Uromyces phaseoli, Race 0. The inhibitor solutions were prepared in 0.01% Tween 20, with the pH adjusted to 7.0. Control plants without inhibitor were sprayed similarly and were allowed to dry before inoculation with the pathogen. After inoculation with rust uredospores (25 mg/100 ml of 0.01% Tween 20) all plants were placed in dew chambers (100% relative humidity) for 16 hours at 19° C. in total darkness. After exposures to inhibitors and uredospores, all plants were returned to the greenhouse and arranged randomly. Disease severity was evaluated 7 days after inoculation by counting foliar lesions. In control plants and those treated with low concentrations of DFMO, uredospores were collected randomly from each treatment to determine percent germination and pathogenicity. For determination of germination, spores were dusted onto Petri plates containing 10 mM 2-(N-morpholino)ethanesulfonic acid (Mes) at pH 7.0, 3 mM $CaCl_2$, 2 mM $MgSO_4$, and 1% purified agar, and incubated for 3 hr at 19° C. in the light.

Each exposure consisted of 12 plants in six replicate pots. All experiments were repeated at least once, with similar results.

RESULTS (See Tables 1, 2 and 3 at the end of Specification)

Figure 1:
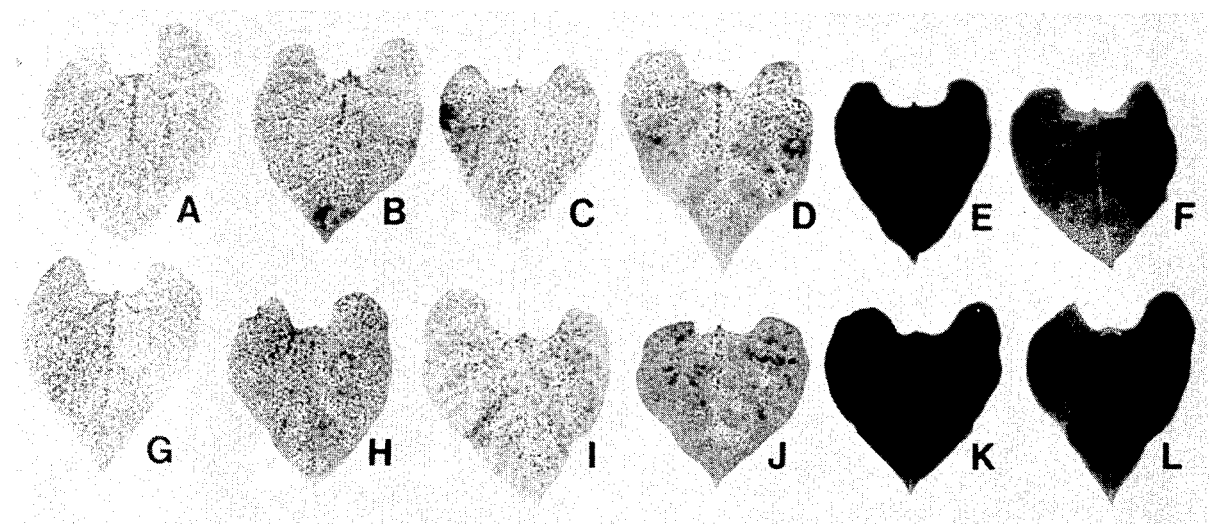
FIG. 1 shows the severity of symptoms of rust disease induced by inoculation of unifoliolate leaves of pinto beans with uredospores of Uromyces phaseoli preceding (A-F) and following (G-L) DFMO treatments. DFMO treatments were at 0, 0.01, 0.05, 0.1, 0.5, and 1.0 mM, in A-F and G-L, respectively.

Foliar lesions characteristic of infection by Uromyces phaseoli uredospores were apparent on control plants without inhibitor within 4-5 days after inoculation and attained their maximal size after 10-12 days. Abundant lesions occurred in the control plants, while plants with pre- or postinoculation exposures to increasing concentrations of DFMO developed progressively fewer lesions (FIG. 1). No disease symptoms could be detected on plants treated with DFMO at 0.5 mM or higher. At the lower concentrations, inhibition of uredial development was more pronounced on plants given postinoculation exposures to the inhibitors. In such cases, uredial appearance was delayed for 2-6 days in DFMO-treated plants, and the extent of delay was dose-dependent. Increasing the concentration of DFMO from 0.01 to 0.25 mM resulted in a gradual decrease in lesion number and disease severity. The $ED^{50}$ was found to be at 0.05 mM and 0.025 mM for pre- and postinoculation exposure to DFMO, respectively. In contrast, alpha-difluoromethylarginine was ineffective in reducing infection, even at 5.0 mM. The average numbers of lesions per square centimeter and per leaf produced by pre- and postinoculation exposures to different concentrations of both the inhibitors are summarized in Table 1. Uredospores collected from plants treated with low concentrations of DFMO and alpha-difluoromethylarginine show no decrease in germination or pathogenicity.

Figure 2:
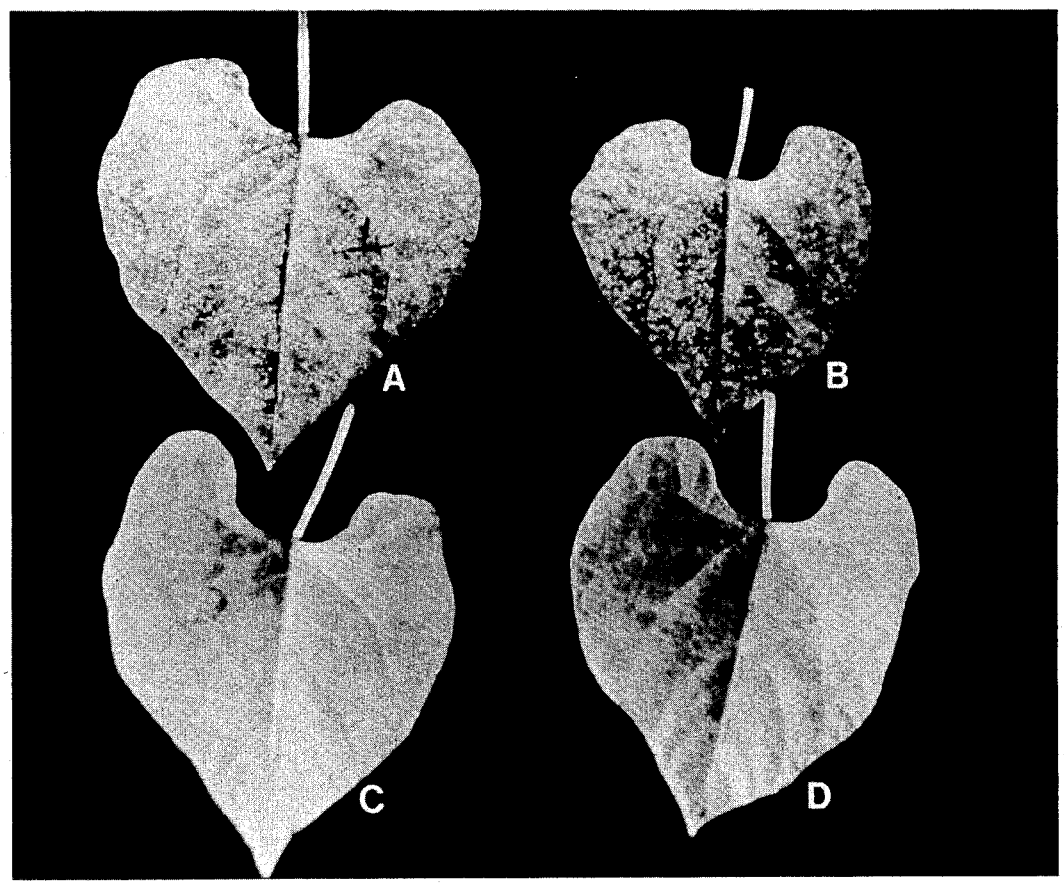
FIG. 2 shows the transfer of the protective effect from sprayed to unsprayed regions of the leaf. Pre- and postinoculation treatments in control (A and B) and 1.0 mM DFMO (C and D), respectively. T, treated side; UT, untreated side.

The protective effects of DFMO are not limited to the region of application, indicating translocation of either DFMO or some substance formed as a result of its application. Thus, when the petiolar or apical half of a unifoliolate leaf was treated with 1 mM DFMO and inoculated with uredospores, the other half was also protected against infection. Transfer of the protective effect was better from leaf base to leaf apex than in the reverse direction. In the half-leaf treatment experiments, postinoculation treatment was once again somewhat more effective than preinoculation exposures to DFMO. Similar translocated protective effects were noted when a longitudinal half or the unifoliolate leaf up to the midvein was treated with DFMO (Table 2; FIG. 2).

In further experiments, plants that had been treated with DFMO and pathogen were reinoculated with pathogen after 1 week, at a time when disease symptoms were apparent on the unifoliolate leaves. The number of lesions on the newly emerged trifoliolate leaves was considerably reduced in plants previously treated at 0.05, 0.1, 0.5, and 1.0 mM DFMO, while 5.0 mM afforded complete protection (Table 3).

Figure 3:
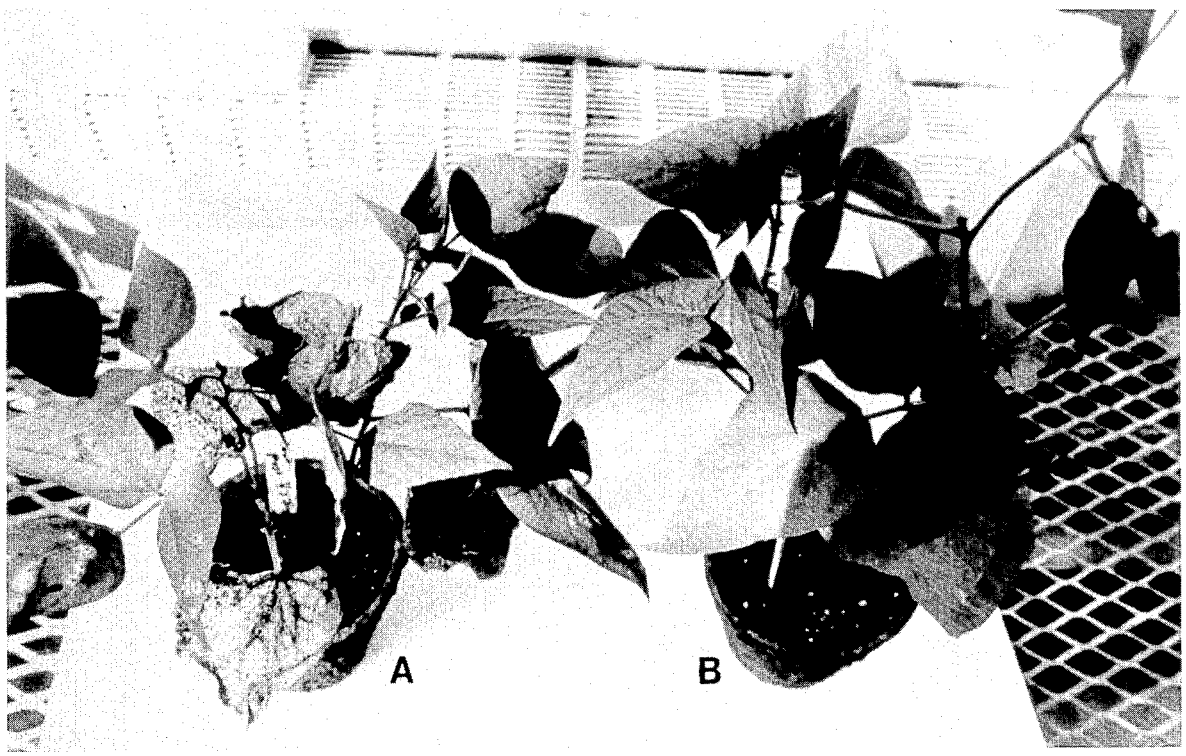
FIG. 3 shows the appearance of 2-week-old bean plants after postinoculation exposures to control (B) and 5.0 mM DFMO (A) sprays.

Plants sprayed with DFMO at all concentrations looked healthy, exhibiting no malformation or reduction in growth rate. By contrast, unprotected, infected plants showed a marked reduction in height (FIG. 3).

DISCUSSION

Polyamines are now regarded as essential for normal growth and development in bacteria (Tabor et al. Supra), fungi (Tabor et al. Supra; Tabor, C. W. (1981) Med. Biol. vol. 59, 272L14 278), higher plants (Cohen, E., Arad, S., Heimer, Y. M. & Mizrahi, Y. (1982) Plant Physiol. vol. 70, 540–543; Galston, A. W. (1983) BioScience vol. 33, 382–388; Slocum, R. D., Kaur-Sawhney, R. & Galston, A. W. (1984) Arch. Biochem. Biophys. vol. 235, 283–303), and mammals (Mamont, P. S., Duchesne, M. C., Grove, J. & Bey, P. (1978) Biochem. Biophys, Res. commun. vol. 81, 58–66). The diamine putrescine is produced from arginine and ornithine via the rate-limiting enzymes ADC and ODC, respectively (Tabor et al. Supra). Bacteria and higher plants have both the ADC and ODC pathways (Tabor et al. Supra; Slocum et al. Supra), while fungi are largely limited to the ODC pathway (Tabor (1981) Supra; Whitney, P. A. & Morris, D. F. (1978) J. Bacteriol. vol 134, 214–220; Paulus, T. J. & Davis, R. H. (1981) J. Bacteriol. vol 145 14–20), with occasional indications of a biodegradative form of ADC (Stevens, L. & Winther, M. D. (1979) Adv. Microb. Physiol. vol 19, 63–148; Uhlemann, A. & Reinbothe, H. (1977) Biochem. Physiol. Pflanz, vol 171, 85–92). The recent availability of DFMO (Metcalf, B. W., Bey, P., Danzin, C., Jung, M. J., Casara, P. & Vevert, J. P. (1978) J. Am. Chem. Soc. vol. 100, 2551–2553) and alpha-difluoromethylarginine (Kallio, A., McCann, P. & Bey, P. (1981) Biochemistry vol. 20, 3163–3166) as specific enzyme-activated "suicide inhibitors" of ODC and ADC, respectively, has made it possible to pinpoint which of these pathways operates in a variety of physiological responses attributable to polyamines (Slocum et al. (1984) Supra). S-Adenosyl methionine decarboxylase, an enzyme important for furnishing aminopropyl groups for transfer to putrescine to make spermidine and spermine (Tabor et al (1985) Supra), has been detected in many fungal extracts. It has been purified from Saccharomyces cerevisiae (Poso, H., Sinervirta, R. & Janne, J. (1975) Biochem. J. vol. 151, 67–73) and shown to be activated by putrescine (Stevens et al. Supra). Thus, fungal pathways for polyamine biosynthesis beyond putrescine seem to resemble those in mammals and higher plants.

DFMO was introduced as an anticancer drug (Metcalf et al. (1978) Supra). Studies on its relation to polyamine depletion (Slocum et al. (1984) Supra; Marton, L. J., Oredsson, S. M., Hung, D. T. & Deen, D. F. (1983) in Advances in Polyamine Research, eds. Bachrach, U., Kaye, A. & Chayen, R. (Raven, N.Y.), vol. 4, 33–40) have confirmed ODC as the biochemical locus of its effect. In fungi (Rajam et al. (1985) Supra) and in higher plants (Berlin, J. & Forche, E. (1981) Z, Pfanzenphysiol. vol. 101, 277–282) it has been found to cause some enlargement of cell diameter, although its major effect is clearly inhibition of cell division (Cohen et al. (1982) Supra). In fungi, use of both specific mutations and enzyme inhibitors has shown the importance of polyamines not only for growth (Tabor et al. (1985) Supra; Slocum et al. (1984) Supra; Whitney et al. (1978) Supra; Cohn, M. S., Tabor, C. W. & Tabor, H. (1978) J. Bacteriol. vol. 134, 208–213) but also for meiosis and sporulation (Tabor et al. (1985) Supra; Brawley, J. V. & Ferro, A. J. (1979) J. Bacteriol. vol. 140, 649–654).

Our experiments show that DFMO protects bean plants against infection by uredospores of *Uromyces phaseoli*. Previous data (Rajam et al (1985) Supra) and current experiments (unpublished) indicate effective inhibition of other phytopathogens in vitro. Since 400 ul of 0.25 mM DFMO applied to a single leaf gives complete protection against infection, we estimate that at a spray rate of 100 gallons to the acre (940 liters/hectare), about 25 g per acre would be adequate for protection of a bean crop in the field. In view of the low toxicity of DFMO (Tabor et al. (1985) Supra), this level of application should pose minimal problems for animals and humans. Furthermore, the lack of effectiveness of alpha-difluoromethylarginine underscores the specificity of DFMO action and explains the lack of toxicity of DFMO to green plants.

The translocatability of the protective effect of DFMO could be due to the movement of DFMO, a DFMO metabolite, or an induced antifungal compound such as a phytoalexin. The fact that postinoculation application of DFMO was more effective than preinoculation speaks, however, against any indirect effect, since some time would have to elapse for metabolic changes to occur.

On the basis of these experiments, we believe that DFMO and other inhibitors of enzymes in the polyamine biosynthetic pathway may prove to be applicable to the alleviation or prevention of crop losses due to phytopathogenic fungi.

For example, the discoveries and teachings were validated by control of the bean rust fungus, *Uromyces appendiculatus* [Pers.] Unger. (*Uromyces phaseoli* L.) on Pinto bean (*Phaseolus vulgaris* L. cv Pinto) The ED50 for control of bean rust in pre- and postinoculation sprays of DFMO separated by 16 hours was 0.05 and 0.025 mM, respectively, whereas concentrations as high as 5 mM had no apparent effect on growth and development of the plant. Furthermore, DFMO conferred protection on unsprayed parts of treated plants, suggesting the DFMO was translocated from the sprayed to the unsprayed areas of the plant, or that DFMO induced the formation of another translocatable antifungal agent. DFMA was ineffective in controlling the bean rust pathogen, which substantially confirmed that the sole or major pathway of PA biosynthesis in the fungus is via ODC and that PAs are required for growth and development of fungi.

THE TEACHINGS OF THE PRESENT INVENTION APPLIED TO VERTICILLIUM WILT OF TOMATOES

The teachings of the present invention also apply to the suppression of Verticillium wilt of tomato by difluoromethylornithine (DFMO). It functions as a suicidal inhibitor of polyamine biosynthesis in the Verticillium wilt but not in the tomato plant.

Difluoromethylornithine (DFMO), is a specific inhibitor of polyamine biosynthesis via ornithine decarboxylase, retarding mycelial growth of *Verticillium dahliae in vitro* at concentrations as low as 5 micromolar. This inhibition could be reversed by putrescine, indicating that the mechanism of inhibition was by prevention of polyamine biosynthesis in the mycelium. Post-inoculation foliar application of DFMO delayed the appearance of symptoms of Verticillium wilt, and increasing doses of the inhibitor reduced the severity of the disease. These results indicate that it may be possible to control Verticillium wilts with target-specific inhibitors, such as DFMO.

Rajam and Galston, as reported in Plant Cell Physiol. vol. 26, 683–692 investigated the effects of DFMO and DFMA on mycelial growth of several fungal plant pathogens in Petri dishes. They found that these materials inhibited vegetative growth of the fungi, and that this inhibition could be reversed by the addition of polyamines such as putrescine or spermidine to the culture media. This is background to the invention described herein and also reported to the public in Plant Cell Physiol. vol 26, 283–692. The effects of DFMO and DFMA on bean rust, caused by *Uromyces phaseoli* was investigated in vivo (the plant to be protected) and it was discovered that DFMO, but not DFMA, would prevent the occurence of this disease.

The effects of DFMO on mycelial growth of *Verticillim dehliae* in vitro, and on symptom expression in Verticillium wilt of tomatoes were studied and the results are supported hereinafter.

MATERIALS AND METHODS

A tomato isolate of *Verticillium dahliae,* TS-1B, was maintained on Czapek-Dox nutrient agar by biweekly transfers from the leading edge of the culture. Spores for inoculation of tomato plants were produced by modified hanging drop techniques (6), incubating the spore cultures at 20° C. under a 16-hour photoperiod provided by 60 uEs-1m.$_2$ of mixed fluorescent and incandescent light. In vitro studies involved Czapek-Dox nutrient salts containing 1% glucose, solidified with 0.75% agarose (IBI Inc, New Haven, Conn), and supplemented with either inhibitors and/or putrescine added to the molten medium by filtration through 0.45 u filters. Mycelial growth was determined in 6 cm. Petri dishes containing 7.5 ml of the appropriate culture medium. Radial growth was determined after 8 days incubation in darkness at 20° C. by averaging measurements made at right angles across the diameter of the developing colonies.

Tomato seedlings, *Lycoperisicon esculentum* L. cv Bonny Best were cultured in 4" pots of Boyce Thompson potting soil under standard greenhouse conditions involving a 16-hour photoperiod provided by a mixed bank of fluorescent and incandescent lights, with 23° C. day and 20° C. night temperatures. At the 5-leaf stage, plants were inoculated by application of 5 ml of $10_{10}$ spores/ml per pot (25 propagules per g soil). At the times indicated, plants were sprayed to runoff with either DFMO or DFMA formulated in 0.01% Tween 20, pH 7.0. Control plants were sprayed similarly with Tween 20. Disease expression was evaluated using a subjective scale of 0 to 5, with 0 representing no disease symptoms, and 5 representing a dead plant.

Ornithine decarboxylase and ADCase activity determinations were carried out on 12-day-old mycelium of the fungus cultured on liquid Czapek-Dox medium containing 1% glucose as the carbon source.

Ornithine decarboxylase and ADCase were assayed by the methods of Kaur-Sawhney et al. (4) using D,L-[$1_{-14}$C]ornithine and L-[$U_{14}$C]arginine as substrates for the respective enzymes. Arginase activity was determined by the methods of Schimke (9), using arginine and DFMA as substrates, and 1-phenyl-1,2-propanedione-2-oxime to detect the urea release by the enzyme. Controls for the arginase determinations were boiled mycelial extracts, and results were adjusted to compensate for readings obtained from substrate blanks. Protein determinations were by the Bradfield method (1), using bovine serum albumin as a reference standard. Difluoromethylornithine and DFMA are products of Merrell-Dow, and are available from them. All other reagents were from Sigma Biochemicals. All experiments were replicated 3 times and repeated twice. Variaions within experiments were generally less than 5%.

RESULTS AND DISCUSSION

Radial growth of *V. dahliae in vitro* was reduced by concentrations of DFMO above 5 micromolar (FIG. 4), and this inhibition would be reversed by addition of 1 mM putrescine to the culture medium, indicating that the mechanism of DFMO-induced growth inhibition was probably through inhibition of polyamine biosynthesis via ODC. FIG. 5 shows the inhibition of radial growth of *Verticillium dahliae* by increasing concentrations of DFMO (shaded bars), and reversal of this inhibition by 1 mM putrescine (open bars) (Data from 8-day old cultures). In addition, higher concentrations of DFMO (500 micromolar and above) inhibited pigment synthesis by this fungus, and this inhibition of pigment synthesis could also be reversed by addition of putrescine to the medium. When the inhibitory effects of DFMO and DFMA were compared in vitro, DFMA appeared to inhibit radial growth of the fungus to approximately 50% of that observed with DFMO (FIG. 6). FIG. 5 shows the inhibition of radial growth of *Verticillium dahliae* induced by 500 uM DFMO and DFMA alone and combined, and reversal of this inhibition by 1 mM putrescine. (Data from 8-day old cultures). These results are similar to those obtained by Rajam and Galston (Plant Cell Physiol. (1985) vol. 26, 683–692) with several other phytopathogenic fungi. These authors suggested that this DFMA-induced inhibition might be due to enzymatic conversion of DFMA to DFMO by arginase. We have examined the levels of ODCase, ADCase and arginase in extracts from the vegetative mycelium of *V. dahliae,* and our results (Table 4) would seem to indicate that this may indeed be the case.

Both isolates of *V. dahliae* examined contained substantial levels of ODCase activity and little or no ADC activity. The apparent ADCase activity, if indeed it was ADCase activity, was extremely low, and this small amount of apparent activity could have been due to other aspects of arginine metabolism. When assayed with arginine, extracts from the vegetative mycelium of tomato isolates of *V. dahliae* contained detectable arginase activity (Table 4). The enzyme was also capable of generating urea from DFMA (Table 4), and, in the process, presumably converting DFMA to DFMO as suggested by SLocum and Galston (Slocum, R. D. and Galston, A. W. (1985) Arginase-mediated hydrolysis of DFMA to DFMO in vivo) (Plant Physiol. vol. 77 (Supplement):45). Although the levels of arginase detected in the mycelium were low, this activity is apparently adequate to convert sufficient DFMA to DFMO for partial inhibition of in vitro radial growth of the fungus. The fact that the inhibitory effects of DFMA were not additive when both DFMO and DFMA were incorporated into the culture medium also suggests that the in vitro effects of these two materials are due to inhibition at the same metabolic site.

Figure 6:
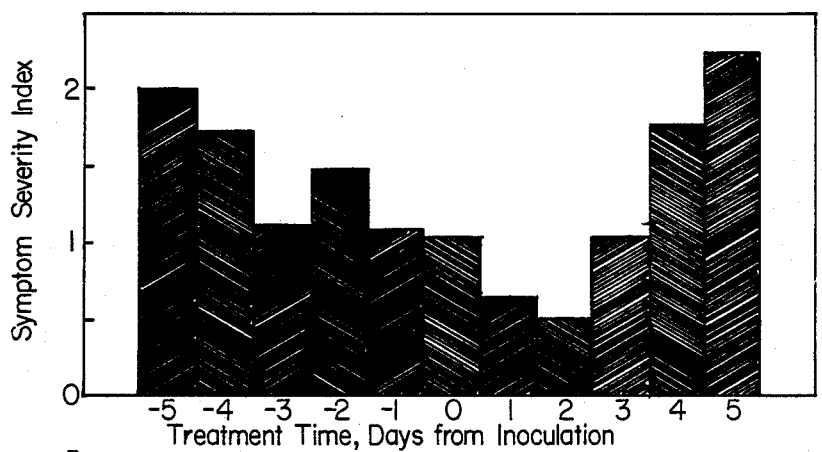
FIG. 6 shows the influence of treatment time on the effects of 5 mM DFMO on Verticillium wilt symptoms in Bonny Best tomato 21 days after inoculation.
Figure 7:
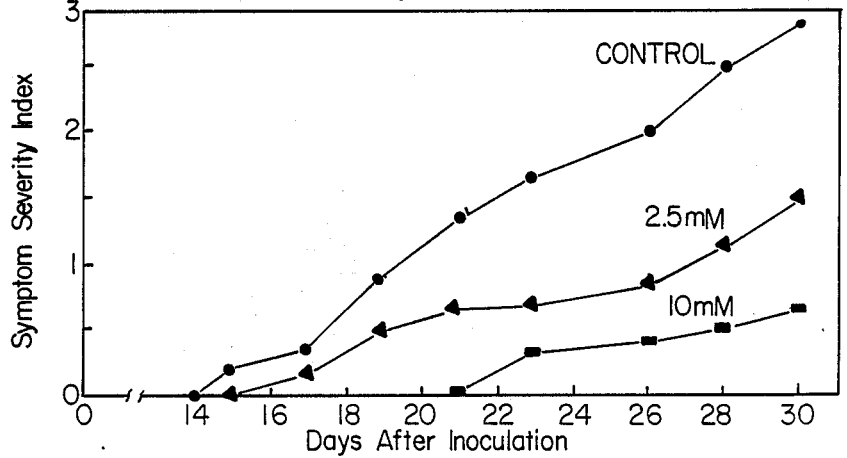
FIG. 7 shows inhibition of the disease progress curve for Verticillium wilt of Bonny Best tomato by 2.5 and 10 mM foliar application of DFMO.

Our firs in vivo investigation involved attempting to determine the optimal timing of treatmennt with respect to inoculation to obtain maximum suppression of the symptoms of Verticillium wilt. This experiment indicated that, as has been observed with bean rust (Supra), the most effective times for application of the inhibitor were 24-48 hours post-inoculation (FIG. 6). FIG. 6 shows the influence of treatment time on the effects of 5 mM DFMO on Verticillium wilt symptoms in Bonny Best tomato 21 days after inoculation. Using this information, we examined disease progress in plants treated with two levels of DFMO 24 hours after inoculation with *V. dahliae*. The results of this experiment (FIG. 7) indicated that DFMO, at both 2.5 mM and 10 mM suppressed symptoms of Verticillium wilt of tomato compared to controls. FIG. 7 shows inhibition of the disease progress curve for Verticillium wilt of Bonny Best tomato by 2.5 and 10 mM foliar application of DFMO and each data point represents an average of 15 determinations. Our results also indicated that increasing the concentration of DFMO from 2.5 to 10 mM delayed the onset of symptom expression up to 7 days. In a similar series of experiments, it was determined that DFMA, at concentrations up to 10 mM, did not alter either symptom severity nor time of symptom expression in this disease. Although not investigated, the ineffectiveness of DFMA in vivo can probably be attributed to binding of the material to tomato ADC, rendering the DFMA unavailable to the arginase of the pathogen. When applied to uninoculated tomato plants at concentrations up to 20 mM, DFMO had no apparent effects on the growth and development of the plants for the duration of the 28-day observation period.

The results of these and other studies indicate that the in vitro sensitivity of phytopathogenic fungi to DFMO varies widely, and may not be a reliable indicator of the potential efficacy of the materials for disease control. The results of our in vivo experiments indicate that target-specific inhibitors of polyamine biosynthesis, like DMFO, may prove to be useful for control of fungal vascular diseases such as Verticillium wilt. These results also clearly indicate that inhibitors such as DFMO can effectively suppress disease symptoms even when applied to a part of the host plant that is spatially separated from the site of infection.

THE TEACHINGS OF THE PRESENT INVENTION APPLIED TO THE PROTECTION OF WHEAT AGAINST LEAF AND STEM RUST AND POWDERY MILDEW DISEASES

Experiments with *Puccinia recondita, P. graminis f. sp. tritici*, and *Erysiphe graminis* on wheat successfully validated the discoveries and teachings of the present invention. Stem and leaf rust and powdery mildew diseases of wheat are important economically worldwide. In the U.S., leaf rust alone caused losses of 72, 30 and 143 million bushels of winter wheat in 1983, 1984 and 1985, respectively; stem rust caused losses of about 0.6, 6.8, and 3.1 million bushels of winter wheat during the same period and destroyed 5 to 20% of the wheat crop in the southeastern U.S. in 1974 (8). Losses from powdery mildew as high as 45% have been reported in England, India, and New Zealand (2) and as high as 25% in the southern U.S.

Recently, we undertook studies on the effects of DFMO and DFMA on the control of leaf and stem rusts and powdery mildew of wheat, caused by the biotrophic parasites *Puccinia recondita* Rob. ex Desm. f. sp. *tritici*, *P. graminis* f. sp. *tritici* E. & H., and *Erysiphe graminis* DC., respectively. The specific objectives were to determine the response of these important pathogens to inhibitors of PA biosynthesis and to provide information on their mechanism of action.

Wheat seedlings (*Triticum aestivum* L. cv. Little Club) were grown in Cornell Mix (1) in a greenhouse at 19° C. When 10 days old, the seedlings were sprayed with solutions of DFMA or DFMO at concentrations of 0.01 to 1.0 mM in 0.01% Tween 20 adjusted to pH 7.0 before and after inoculation with uredospores of the *P. graminis* f. sp. tritici or *P. recondita* f. sp. tritici, as described earlier herein. Control plants were sprayed with 0.01% Tween 20, and all plants were allowed to dry before inoculation with rust uredospores (25 mg./100 ml. 0.01% Tween 20). Inoculated plants were then placed in incubation chambers at 100% R.H. for 16 hours at 19° C. in total darkness. Post-inoculation treatments were made about 1 hour after plants were removed from the incubation chambers. Plants were then returned to the greenhouse and randomly arranged on the benches. Infection was evaluated 6-8 days later by counting the number of developing uredia per plant.

With wheat powdery mildew (*E. graminis*) 10-day-old seedlings were sprayed with solutions of DFMA or DFMO from 0.01 to 5.0 mM before and after inoculation of the plants with conidia. Inoculation occurred naturally in the greenhouse by distributing infected plants among the experimental plants for 24 hours. Infection was evaluated 10 days after inoculation by counting mildew colonies.

RESULTS

Wheat stem rust infection was controlled more effectively by DFMO than by DFMA and post-inoculation treatment provided greater control than pre-inoculation treatment (Table 5). With DFMO, the ED50 was 0.56 mM for pre-inoculation treatment, but was only 0.03 mM for post-inoculation treatment. DFMA was relatively ineffective for disease control, as had been shown earlier with bean rust.

Both pre- and post-inoculation treatments with DFMO were effective controls for wheat leaf rust with respective ED50's of 0.026 mM and less than 0.008 mM (Table 6). Concentrations as low as 0.10 mM DFMO provided more than 90% control. Post-inoculation treatment with DFMA was very effective with an ED50 of 0.042 mM.

Control of powdery mildew by treatment with inhibitors was somewhat less complete than for rusts (Table 7). DMFO was generally more effective before inoculation than after with respective ED50's for pre-and postinoculation treatments of 0.077 and 0.07 mM. DMFA at concentrations up to 5 mM was ineffective in controlling infection and neither inhibitor had any apparent effect on the growth of wheat plants.

DISCUSSION

Among the features of the DFMO/plant/pathogen interaction that are of special interest are the wide differences in the susceptibility of phytopathogenic fungi to DFMO and the differences in responses observed in vitro and in vivo. For example, Rajam and Galston (Plant Cell Physiol. (1985), vol. 26, 683–692) showed that both PA biosynthetic inhibitors, DFMO and DFMA, inhibited mycelial growth of Botrytis sp., B. cinerea Pers. ex F., Rhizoctonia solani Kuehn, and Monilinia fructicola (Wint.) in vitro. Addition of PAs reversed the inhibitory effect of both difluoro compounds in Botrytis sp. and Monilinia fructicola. However, in Plant Cell Physiol. (1985), vol. 26, 683–692, DFMA was a more effective inhibitor of fungal growth than was DFMO. Inhibition by DFMA suggests that ADC may also be present in those fungi tested, or that DFMA may be converted to DFMO by arginase (Plant Physiol. (1985), vol 77 (Supplement); 45), whereby DFMO would still be the inhibitory agent. Thus in the presence of an active arginase, DFMA would inhibit both ADC and ODC, whereas DFMO would only inhibit ODC. Nevertheless, DFMA was always less effective than DFMO in experiments in vivo, but it was sufficiently effective, especially for wheat leaf rust, to invoke the possibilities of an active arginase in the plant or the pathogenn or of the induction of a plant resistance mechanism unrelated to effects of DFMO or DFMA on the pathogen itself. These mechanisms might help to explain the relative insensitivity of many fungi to DFMO in vitro.

Another unresolved anomaly in the DFMO/plant/pathogen system if ODC blockage is postulated as a control mechanism is why a pre-inoculation treatment is less effective than post-inoculation treatment with most pathogens studied to date. E. graminis may be an exception but the method of inoculation blurs the distinction between pre- and post-inoculation treatments. One or more or several alternatives may account for the differences in pre- and post-inoculation treatment. One is that DFMO that penetrates the leaf after a pre-inoculation treatment would react with and inhibit some portion of the endogenous ODC of the plant cell, reducing the effective titer of DFMO occurring before spore application would render the treatment less effective. A third alternative may be more related to differentiation of the sporeling than to the germination process per se. When uredospores of U. appendiculatus, a biotrophic parasite, germinate and grow on the surface of the leaf, the presence of stomata induces the differentiation of appressoria, infection pegs, and vesicles. Spores germinated on agar alone do not differentiate, but U. appendiculatus sporelings differentiate on artificial media in the presence of potassium salts and other treatments or factors (Staples, R. C. and Macko, V. (1984) in: Cereal Rusts vol. 1; Bushnell, W. R. and Roelfs, A. J. (eds.) pp 255–289, Accademic Pross.) However, in preliminary experiments, there was no difference in the response of U appendiculatus uredospores to DFMO or DFMA in the presence or absence of added potassium salts.

Perhaps the most puzzling question relates to the presence of PAs in the pathogen and in the plant cell during the infection process. When applied to the plant, DFMO can inhibit the process of infection or early fungal development. This is not the case for germination of U. appendiculatus uredospores in vitro, where DFMO or DFMA are much less inhibitory to germination than exogenously applied PAs, such as spermidine. One obvious explanation for effects on the leaf surface is that the infection process is reduced by DFMO inhibition of ODC in fungal and plant cells. But since higher plants also have an ADC pathway, there should be a sufficient intracellular PA titer for normal growth and development of the plant to occur. The explanation may involve separate compartmentation of the PAs produced by ADC and ODC, as indicated by evidence specifying a nuclear locale for ODC and a cytosolic location for ADC in higher plants (Arch. Biochem. Biophys. 235: 283–303) or induction of a resistance mechanism unrelated to the inhibition of PA biosynthesis itself. Obviously, these and other questions must be answered before the mechanism of control of plant pathogenic fungi by inhibitors of PA biosynthesis can be understood.

Site-directed control of even a few plant diseases, based on differences in pathways of PA biosynthesis between the host and the pathogen may not only help in understanding pathogenesis but also provide an important approach to the control of phytopathogenic fungi.

KINETIC STUDIES ON THE CONTROL OF THE BEAN RUST FUNGUS

It has been established, through the use of genetic mutants and specific chemical inhibitors, that polyamines are essential for optimal growth and development in bacteria and fungi, higher plants, and mammals. The formation of PAs in bacteria and higher plants may proceed through either of two enzymes, e.g., ADC or ODC, while only the ODC pathway operates in many fungi. DFMA and DFMO which specifically and irreversibly block ADC and ODC, respectively, have been used to specify the initial route of Put biosynthesis in many organisms. Since Spd and Spm are formed from Put, effective blockage of Put formation can deprive the organism of all PA. The presence of but a single Put biosynthetic pathway in fungi (via ODC) suggested a possible approach to the use of DMFO as a protectant or possibly a chemotherapeutic agent in the prevention of certain types of fungal pathogenesis in higher plants.

In growth experiments on defined media with several phytopathogenic fungi, we observed that DFMO is an effective inhibitor of mycelial growth, and that such inhibitions are completely reversed by application of Put or Spd to the culture medium. In a recent paper, we reported on the remarkable efficacy of DFMO as a protectant of bean plants against infection caused by uredospores of Uromyces phaseoli, Race 0, the common bean rust fungus. Not only could we obtain complete protection by as little as 400 ul of 0.5 mM DFMO applied to a single unifoliolate leaf, but DFMO was found to confer protection as well on unsprayed parts of treated plants, indicating the translocation of some protective effect from the sprayed areas. The present work extends that study, reporting on the kinetics and reversibility of the DFMO effect.

Unifoliolate leaves of 10-day-old greenhouse-grown bean seedlings (Phaseolus vulgaris cv Pinto) were sprayed with DFMO or DFMA in 0.01% Tween-20 at pH 7.0 before or after inoculation with uredospores of U. phaseoli L., Race 0. Control plants were sprayed similarly with Tween-20 without inhibitor. In experiments involving the reversal of DFMO effects, we utilized 0.05 mM DFMO (which yielded approximately 50% inhibition of uredial development) together with 0.01, 0.1 and 1.0 mM Put of Spd. After inoculation with rust uredospores (25 mg/100 ml of 0.01% Tween 20), all plants were placed in dew chambers (100% RH) for 16 hr at 19° C. in total darkness, as previously described. Plants were returned to the greenhouse and arranged randomly following exposures to inhibitor and uredospores. Disease severity was evaluated 7 days after inoculation by counting the lesions on the leaf.

PA analysis was performed on leaf samples collected from inhibitor-sprayed bean plants. Leaf samples were ground in prechilled mortars with 10% (w/v) $HClO_4$ at a ratio of 200 mg fresh weight leaf per ml $HClO_4$. Homogenates were centrifuged at 26,00 g for 20 minutes at 4° C. The clear supernatant fractions were used for dansylation according to a procedure previously described. Briefly, 0.4 ml of freshly prepared dansyl (Diaminonaphthylsulfonyl)-Cl (Sigma), 5 mg/ml in acetone, and 0.2 ml of saturated $Na_2CO_3$ were added to 0.2 ml of the supernatant fraction. The dansylated PA were extracted with 0.25 ml benzene and the clear benzene layer was used for PA determinations by TLC on LK6D high resolution silica gel plates (Whatman). After development in chloroform:triethylamine (25:2 v/v) for about 1 hour and location by fluorescence under a UV lamp, the dansylpolyamine bands were scraped off, eluted in 4 ml of ethyl acetate and quantified with an Aminco-Bowman fluorimeter.

Figure 8:
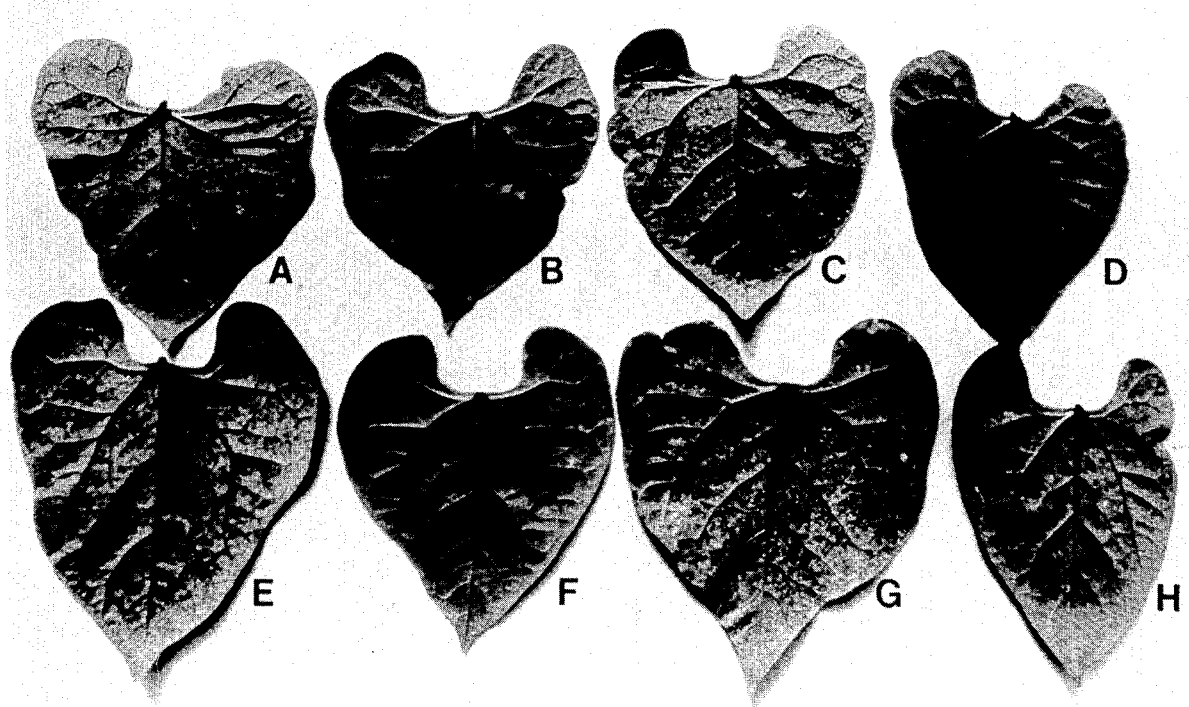
FIG. 8 shows the kinetics of pathogen inhibition following postinoculation exposures to 1.0 mM DFMO. Unifoliolate leaves of controls (A, C, E, and G) and DFMO treatments (B, D, F, and H) on 1, 2, 3, and 4 days after inoculation with uredospores of U. phaseoli, respectively.
Figure 4:
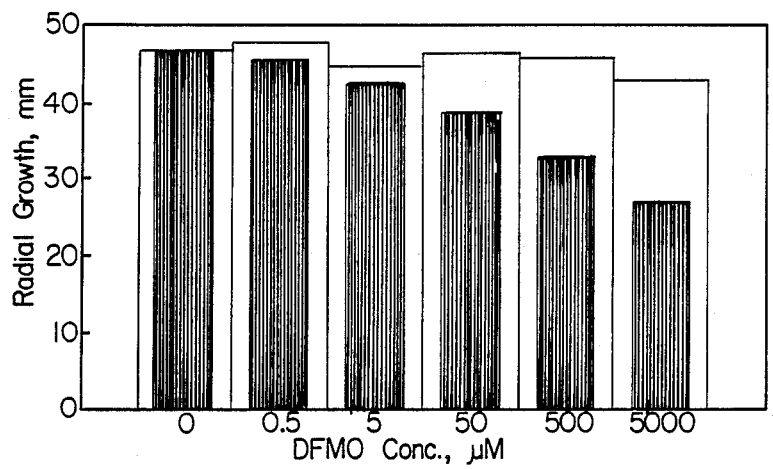
FIG. 4 shows inhibition of radial growth of Verticillium dehliae by increasing concentrations of DFMO (shaded bars), and reversal of this inhibition by 1 mM putrescine (open bars). Data from 8-day old cultures.
Figure 5:
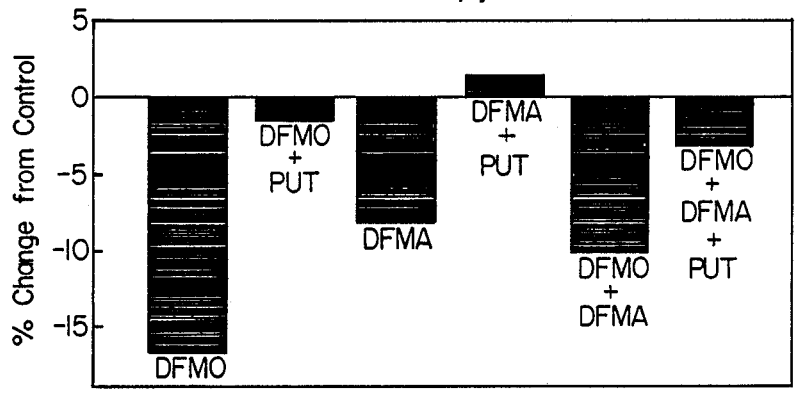
FIG. 5 shows inhibition of radial growth of Verticillium dahliae induced by 500 uM DFMO and DFMA alone and combined, and reversal of this inhibition by 1 mM putrescine. Data from 8-day old cultures.

We reported previously that DFMO at 0.5 mM or higher gives complete protection against the pathogen in both pre- and postinoculation exposures when inoculation and treatment are separated by 24 hours. In the present work, we determined the effect of varying delays in postinoculation application of DFMO on the extent and course of pathogenesis. Test plants were exposed to 1.0 mM DFMO either 1, 2, 3, 4, or 5 days after inoculation with uredospores of the pathogen. Complete protection against the pathogen was found when DFMO was first applied up to 3 days after inoculation (FIG. 8). Disease symptoms occurred when the interval between inoculation and DFMO application was 4 or 5 days, although the number of lesions was significantly reduced below control (unprotected) values (Table 8).

In vitro, uredospore germination starts 30 minutes after incubation at 19° C. in the light, and the germ tube reaches an effective size for leaf penetration within 3 hours in the presence of 10 mM Mes (pH 7.0), 3 mM $CaCl_2$, 2 mM $MgSO_4$, and 1% purified agar. We attempted to visualize spore germination on the surface of the unifoliolate bean leaf with crystal violet, 1 day after spore inoculation. The plants had been sprayed with DFMO at 0, 0.01, 0.05, 0.1, 0.5, and 1.0 mM 1 day before inoculation. Germination was normal on control leaves, completely inhibited on leaves treated with more than 0.5 mM DFMO, and partially inhibited at lower concentrations of DFMO.

To determine whether the effect of DFMO was related to inhibition of PA biosynthesis, we conducted experiments to determine the effect of PA application, alone or in combination with 0.05 mM DFMO (which yielded approximately 50% inhibition of uredial formation), on the severity of the disease. There were generally no significant differences between controls and PAs alone except at 1 mM Put, which reduced the number of lesions by about one-third. This is probably due to the well known toxic effect of mM Put. The number of lesions was reduced by 70% in plants exposed to 0.05 mM DFMO alone; when Spd was supplied 1 hour after DFMO, the inhibition conferred by DFMO was substantially reduced (Table 9).

The effect of DFMO and DFMA sprays (0.01, 0.1, and 1.0 mM) on PA titers was also examined. Unifoliolate leaves were sprayed in the usual way and examined 1 and 3 days later, while the first trifolioloate leaves, unexpanded ata the time of spray and themselves unsprayed, were examined 8 days later. There were no significant reductions of PA levels in any of the treated leaves; in fact, Put and Spd titers were increased by the highest concentration of DFMO (unpublished data). This appears to be due t the paradoxical promotion of ADC activity by DFMO. There was no effect of DFMO or DFMA sprays on the growth of the plants.

Thus, in the absence of any depression in the PA titer of the host plant, we reason that the prtective effect of DFMO against the fungus results in part from its persistence on the surface of the leaf, where fungal spores germinate and initiate growth. Since rust uredosporelings contain progressively higher Spd as their growth and differentiation progresses, it is reasonable to believe that PA deprivation caused by DFMO would inhibit both processes. The translocatability of the protective effect of DFMO indicates that this substance may also initiate internal protective metabolic changes that are not reflected in the PA titer of the host plant.

OAT STEM RUST

See Table 10 for the effect of DFMO and DFMA on infection by oat stem rust (*Puccinia graminis* fsp avenae) The application of DFMO solution at concentrations as low as 0.01 mM (ca. 2.4 mg per liter) provides 50% protection against infection by oat stem rust uredospores of Ogle oat plants. More than 80% protection is provided at 0.20 mM DFMO (ca. 57 mg per liter) and more than 90% protection at 1.0 mM (236 mg per liter). With this pathogen, DMFA was nearly as effective as DFMO, probably because of conversion of DFMA to DFMO by the enzyme arginase in the plant or in the fungal spore.

CORN RUST

See Table 11 for the effect of DFMO and DFMA on infection by corn rust (Puccinia sorghi), The application of DFMO solution at a concentration of less than 0.1 mM (ca. 24 mg per liter) provided 50% protection against infection by corn rust uredospores. Nearly 90% control of the disease was achieved at 0.16 mM DFMO (ca. 37 mg per liter). DFMA was essentially ineffective up to 0.20 mM, but about 50% control was achieved at 1.0 mM (ca. 240 mg per liter).

APPLE POWDERY MILDEW

See Table 12 for the effect of DFMO and DFMA on infection of apple powdery mildew (*Podosphaera leucotricha*). Protection of apples from infection by the apple powdery mildew fungus was about 50% after treatment with 1 mM DFMO solution. About 80% control was achieved with 10 mM DFMO. DFMA applications were essentially ineffective in the control of this pathogen.

OTHER STUDIES

See Table 13 for the effect of DFMO or DFMA on germination and differentiation of bean rust uredospores. The relative ineffectiveness of DFMO or DFMA to control germination of bean rust uredospores demonstrates the need to test plant pathogens on their host plant. At 5 mM, DFMO inhibited germination of uredospores in agar in Petri plates by ca. 50%, and DFMA was slightly less effective. Compare these concentrations in vitro to the great effectiveness of DFMO.

See Table 14 for the effect of DFMA and DFMO on infection by bean powdery mildew (*Erysiphe polygoni*). The bean powdery mildew fungus is controlled ca. 35, 45, and 50% by application of 1, 5 and 10 mM DFMO solutions. The combination of DFMO with DFMA is less effective than DFMO alone.

CUCUMBER ANTHRACNOSE FUNGUS

See Table 15 for the effect of DFMO on radial growth in vitro on cucumber anthracnose fungus (*Colletotrichum lagenarium*). The cucumber anthracnose fungus growing in Czapek's agar in Petri plates is not affected by DFMO up to 5 mM.

See Table 16 for the effect of DFMO and DFMA on infection by cucumber anthracnose (*Colletotrichum lagenarium*). DFMO is not effective in controlling all fungal pathogens of plants. Neither DFMO, DFMA, nor their combination, reduced the infection of National Pickling cucumber plants by the cucumber anthracnose fungus.

The foregoing description has been directed to particular embodiments of the invention in accordance with the requirements of the Patent Statutes for the purposes of illustration and explanation. It will be apparent, however, to those skilled in this art that many modifications and changes will be possible without department from the scope and spirit of the invention. It is intended that the following claims be interpreted to embrace all such modifications and changes.

TABLE 3

Mean number of lesions induced by uredospores of *Uromyces phaseoli* in reinoculated trifoliolate leaves of bean plants

| DFMO, mM | Preinoculation exposure | | Postinoculation exposure | |
|---|---|---|---|---|
| | Lesions per cm$^2$ | Lesions per leaflet | Lesions per cm$^2$ | Lesions per leaflet |
| 0 | 69 ± 6 | 1525 ± 99 | 71 ± 3 | 1402 ± 88 |
| 0.05 | 64 ± 5 | 1458 ± 92 | 59 ± 1* | 1246 ± 73 |
| 0.1 | 55 ± 3 | 1274 ± 120 | 58 ± 4* | 1289 ± 131 |
| 0.5 | 39 ± 7* | 1172 ± 158 | 41 ± 4** | 982 ± 84* |
| 1.0 | 16 ± 2** | 320 ± 22* | 22 ± 2** | 422 ± 13** |
| 5.0 | 0** | 0** | 0** | 0** |

Trifoliolate leaves were reinoculated with pathogen after 1 week, before or after exposure to DFMO, to detect transfer of a protective effect to other parts of the plant. Each value is the mean ± SEM, based on six replicates(one leaf per plant). * and ** denote significant differences from controls at the 5% and 1% level, respectively.

TABLE 4

Activities of ODC, ADC and Arginase observed in extracts from mycelium of 12-day old cultures of *Verticillium dahliae*

| | Enzyme Activity | | | |
|---|---|---|---|---|
| | | | arginase[2] | |
| Isolate | ODC[1] | ADC[1] | ARG | DFMA |
| TS-1B | 395.9 | 1.2 | 11.2 | 7.1 |
| TS-2B | 190.6 | 8.0 | 19.1 | 11.3 |

[1] pM $CO_2$/hr/mg protein
[2] pM urea/hr/mg protein

TABLE 5

Effect of pre- and post-inoculation treatment with DFMA and DFMO on wheat stem rust infection.

| Concentration (mm) | Pre-inoculation | | Post-inoculation | |
|---|---|---|---|---|
| | Uredia/plant | % control | Uredia/plant | % control |
| DFMA | | | | |

TABLE 1

Mean number of lesions induced by uredospores of *Uromyces phaseoli* on unifoliolate leaves of bean plants exposed to DFMO or α-difluoromethylarginine (DFMA) before or after inoculation

| Treatment | | Preinoculation exposure | | Postinoculation exposure | |
|---|---|---|---|---|---|
| Inhibitor | Conc., mM | Lesions per cm$^2$ | Lesions per leaf | Lesions per cm$^2$ | Lesions per leaf |
| None | | 59 ± 4 | 3708 ± 375 | 61 ± 2 | 3091 ± 71 |
| DFMO | 0.01 | 47 ± 6 | 2677 ± 397 | 40 ± 5* | 1888 ± 249** |
| | 0.025 | 34 ± 1** | 2071 ± 103** | 28 ± 2** | 1526 ± 160** |
| | 0.05 | 29 ± 4** | 1712 ± 375* | 17 ± 2** | 1026 ± 131** |
| | 0.075 | 19 ± 2** | 1177 ± 159** | 12 ± 1** | 669 ± 96** |
| | 0.10 | 14 ± 2** | 659 ± 104** | 5 ± 1** | 221 ± 39** |
| | 0.25 | 2 ± 1** | 85 ± 20** | 2 ± 1** | 73 ± 4** |
| | 0.50 | 0** | 0** | 0** | 0** |
| | 1.0 | 0** | 0** | 0** | 0** |
| | 5.0 | 0** | 0** | 0** | 0** |
| DFMA | 1.0 | 51 ± 4 | 3101 ± 217 | 56 ± 3 | 2829 ± 242 |
| | 5.0 | 46 ± 4 | 2928 ± 317 | 50 ± 2* | 2195 ± 169** |

Each value is the mean ± SEM, based on six replicates (one leaf per plant). $ED_{50}$ values were approximately 0.05 and 0.025 mM DFMO for pre- and postinoculation exposures, respectively. * and ** denote significant differences from controls at the 5% and 1% level, respectively.

TABLE 2

Evidence for translocation of a protective effect against bean rust disease from unifoliolate leaves of pinto bean partially treated with 1 mM DFMO

| Treatment | | Preinoculation exposure | | | | Postinoculation exposure | | | |
|---|---|---|---|---|---|---|---|---|---|
| | | Lesions per cm$^2$ | | Lesions per half leaf | | Lesions per cm$^2$ | | Lesions per half leaf | |
| Inhibitor | Conc., mM | Treated side | Untreated side | Treated side | Untreated side | Treated side | Untreated side | Treated side | Untreated side |
| None | | 80 ± 12 | 75 ± 13 | 2379 ± 358 | 2259 ± 399 | 71 ± 7 | 68 ± 8 | 1955 ± 192 | 1869 ± 263 |
| DFMO | 1.0 | 0** | 22 ± 4* | 0** | 617 ± 112* | 0** | 0** | 0** | 0** |

DFMO in 0.01% Tween 20 was applied with an artist's brush to the adaxial surface of one longitudinal half (divided by the midvein) of unifoliolate bean leaves, before or after inoculation with uredospores of Uromyces. Controls were treated similarly with Tween 20 alone. Each value is mean ± SEM, based on six replicates (one leaf per plant). * and ** denote significant differences from control at 5% and 1% level, respectively.

TABLE 5-continued

Effect of pre- and post-inoculation treatment with DFMA and DFMO on wheat stem rust infection.

| Concentration (mm) | Pre-inoculation Uredia/plant | % control | Post-inoculation Uredia/plant | % control |
|---|---|---|---|---|
| 0.00 | 210 | — | 210 | — |
| 0.01 | 192 | 9 | 154 | 27 |
| 0.025 | 167 | 20 | 134 | 36 |
| 0.065 | 168 | 20 | 150 | 29 |
| 0.10 | 165 | 21 | 152 | 28 |
| 0.13 | 193 | 8 | 122 | 42 |
| 0.16 | 186 | 11 | 122 | 42 |
| 0.20 | 172 | 18 | 124 | 41 |
| 1.00 | 148 | 30 | 126 | 40 |
| | Probit = 5.6414−0.1267 log conc. | | Probit = 5.1831−0.1892 log conc. | |
| | DFMO | | | |
| 0.00 | 210 | — | 210 | — |
| 0.01 | 194 | 8 | 134 | 36 |
| 0.025 | 175 | 17 | 117 | 44 |
| 0.065 | 182 | 13 | 94 | 55 |
| 0.10 | 183 | 13 | 51 | 76 |
| 0.13 | 170 | 19 | 49 | 77 |
| 0.16 | 143 | 32 | 40 | 81 |
| 0.20 | 143 | 32 | 37 | 82 |
| 1.00 | 91 | 57 | 17 | 92 |
| | $ED_{50}$ = 0.56 | | $ED_{50}$ = 0.30 mM | |
| | Probit = 4.7971−0.8183 log conc. | | Probit = 3.3695−1.0731 log conc. | |

TABLE 6

Effect of pre- and post-inoculation treatment with DFMA and DFMO on wheat leaf rust infection.

| Concentration (mm) | Pre-inoculation Uredia/plant | % control | Post-inoculation Uredia/plant | % control |
|---|---|---|---|---|
| | DFMA | | | |
| 0.00 | 80 | — | 80 | — |
| 0.01 | 74 | 7 | 49 | 39 |
| 0.025 | 62 | 22 | 40 | 50 |
| 0.065 | 54 | 32 | 37 | 54 |
| 0.10 | 50 | 37 | 39 | 51 |
| 0.13 | 53 | 34 | 42 | 47 |
| 0.16 | 49 | 39 | 41 | 49 |
| 0.20 | 43 | 46 | 42 | 47 |
| 1.00 | 34 | 57 | 18 | 77 |
| | $ED_{50}$ = 0.4337 mM | | $ED_{50}$ = 0.042 mM | |
| | Probit = 4.8738−0.3478 log conc. | | Probit = 4.5554−0.3238 log conc. | |
| | DFMO | | | |
| 0.00 | 80 | — | 80 | — |
| 0.01 | 44 | 45 | 32 | 60 |
| 0.025 | 39 | 51 | 27 | 66 |
| 0.005 | 38 | 52 | 14 | 82 |
| 0.10 | 41 | 49 | 5 | 94 |
| 0.13 | 36 | 55 | 8 | 90 |
| 0.16 | 38 | 52 | 6 | 92 |
| 0.20 | 28 | 65 | 4 | 95 |
| 1.00 | 22 | 72 | 0 | 100 |
| | $ED_{50}$ = 0.0.026 mM | | $ED_{50}$ = 0.008 mM | |
| | Probit = 4.5043−0.3118 log conc. | | Probit = 2.5739−1.1557 log conc. | |

TABLE 7

Effect of DFMO on wheat powdery mildew infection.

| Concentration (mm) | Pre-inoculation Colonies/plant | % control | Post-inoculation Colonies/plant | % control |
|---|---|---|---|---|
| 0.00 | 37 | — | 37 | — |
| 0.01 | 22 | 41 | 30 | 19 |
| 0.025 | 24 | 35 | 26 | 30 |
| 0.065 | 20 | 46 | 20 | 46 |
| 0.10 | 18 | 51 | 12 | 68 |
| 0.20 | 20 | 46 | 12 | 68 |
| 1.00 | 13 | 66 | 9 | 76 |
| 5.00 | 2 | 95 | 4 | 89 |
| | $ED_{50}$ = 0.077 mM | | $ED_{50}$ = 0.070 mM | |
| | Probit = 4.3329−0.5999 log conc. | | Probit = 4.2448−0.6544 log conc. | |

TABLE 8

Kinatics of Inhibition of Pathogenesis Resulting from Postinoculation Application of DFMO to Unifoltolate Leaves of Bean Plants after Different Intervals of Time Unifoliolate leaves were inoculated with uredospores and then, at daily intervals, a different group of plants was sprayed with 0.01% Tween 20 looking or containing 1.0 mM DFMO.

| Time between Spore Isoculation and DFMO Spray d | DFMO Concentration mM | Lesions per $cm^2$ | per leaf[a] |
|---|---|---|---|
| 1 | 0 | 74± 6 | 4673 ± 373 |
| | 1.0 | 0 | 0 |
| 2 | 0 | 69 ± 6 | 4568 ± 398 |
| | 1.0 | 0 | 0 |
| 3 | 0 | 64 ± 4 | 3172 ± 276 |
| | 1.0 | 0 | 0 |
| 4 | 0 | 65 ± 6 | 4419 ± 461 |
| | 1.0 | 41 ± 5[b] | 2330 ± 211[b] |
| 5 | 0 | 69 ± 3 | 3962 ± 217 |
| | 1.0 | 53 ± 4[b] | 3278 ± 326 |

[a]Each value is Mean ± SB, based on six replicates (one leaf per plant).
[b]Significant difference at 5% level.

TABLE 9

Effect of Postinoculation Application of DFMO, and of PAs, Alone or in Combination, on the Severity of Bean Rust Disease on Unifoliate Leaves

| Treatment mM | Lesions per cm[2] | per leaf[a] |
|---|---|---|
| Control | 64 ± 4 | 4104 ± 187 (100)[b] |
| Put, 0.01 | 57 ± 2 | 4013 ± 264 (98) |
| Put, 0.1 | 54 ± 5 | 3189 ± 478 (78) |
| Put, 1.0 | 44 ± 9 | 2698 ± 260 (66) |
| Spd, 0.01 | 56 ± 5 | 3209 ± 360 (78) |
| Spd, 0.1 | 58 ± 6 | 3416 ± 457 (83) |
| Spd, 1.0 | 50 ± 10 | 3926 ± 358 (96) |
| DFMO, 0.05 | 22 ± 4 | 1223 ± 268 (30) |
| DFMO, 0.05 + Put, 0.01 | 30 ± 5 | 1823 ± 289 (44) |
| DFMO, 0.05 + Put, 0.1 | 24 ± 4 | 1440 ± 337 (35) |
| DFMO, 0.05 ± Put, 1.0 | 32 ± 2 | 2009 ± 129 (49) |
| DFMO, 0.05 + Spd, 0.01 | 29 ± 3 | 1678 ± 240 (41) |
| DFMO, 0.05 + Spd, 0.1 | 38 ± 7 | 2366 ± 488 (58) |
| DFMO, 0.05 + Spd, 1.0 | 39 ± 3 | 2334 ± 245 (57) |

[a]Each value is mean ± SB, based on six replicates (one leaf per plant).
[b]Percent of control values are in parentheses.

TABLE 10

Effect of DFMO and DFMA on infection by oat stem rust (*Puccinia graminis* fsp *avenae*)

| Concentration (mM) | Percent control |
|---|---|
| | DFMO |
| 0.00 | — |
| 0.01 | 50.7 |
| 0.025 | 63.2 |
| 0.065 | 65.5 |
| 0.10 | 71.0 |
| 0.13 | 67.9 |
| 0.16 | 77.3 |
| 0.20 | 82.8 |
| 1.00 | 92.9 |
| | DFMA |

TABLE 10-continued

Effect of DFMO and DFMA on infection by oat stem rust (*Puccinia graminis* fsp *avenae*)

| Concentration (mM) | Percent control |
| --- | --- |
| 0.00 | — |
| 0.01 | 40.4 |
| 0.025 | 32.6 |
| 0.065 | 41.9 |
| 0.10 | 53.1 |
| 0.13 | 61.5 |
| 0.16 | 57.0 |
| 0.20 | 63.8 |
| 1.00 | 86.0 |

TABLE 11

Effect of DFMO and DFMA on infection by corn rust (*Puccinia sorghi*)

| Concentration (mM) | Percent Control |
| --- | --- |
| DFMO | |
| 0.00 | — |
| 0.01 | 43.5 |
| 0.025 | 38.4 |
| 0.065 | 37.4 |
| 0.10 | 63.1 |
| 0.13 | 67.7 |
| 0.16 | 88.7 |
| 0.20 | 88.4 |
| 1.00 | 94.9 |
| DFMA | |
| 0.00 | — |
| 0.01 | 13.0 |
| 0.025 | 7.2 |
| 0.065 | 0.0 |
| 0.10 | 0.0 |
| 0.13 | 9.3 |
| 0.16 | 27.1 |
| 0.20 | 14.0 |
| 1.00 | 46.6 |

TABLE 12

Effect of DFMO and DFMA on infection of apple powdery mildew (*Podosphaera leucotricha*)

| Treatment | Percent Control |
| --- | --- |
| Control | — |
| 1 mM DFMO | 45.0 |
| 5 mM DFMO | 48.6 |
| 10 mM DFMO | 81.9 |
| 1 mM DFMA | 0.8 |
| 5 mM DFMA | 28.8 |
| 10 mM DFMA | 0.0 |

TABLE 13

Effect of DFMO or DFMA on germination and differentiation of bean rust uredospores.

| | Germination | | Differentiation | |
| --- | --- | --- | --- | --- |
| Treatment (mM) | % | % Inhibition | % | % Inhibiton |
| 0.0 | 42 | — | 59 | — |
| 0.1 DFMA | 36 | 14 | 46 | 22 |
| 0.5 DFMA | 36 | 14 | 30 | 49 |
| 1.0 DFMA | 31 | 26 | 23 | 61 |
| 5.0 DFMA | 26 | 38 | 18 | 69 |
| 0.0 | 42 | — | 59 | — |
| 0.1 DFMO | 32 | 24 | 46 | 22 |
| 0.5 DFMO | 32 | 24 | 35 | 41 |
| 1.0 DFMO | 32 | 24 | 30 | 49 |
| 5.0 DFMO | 22 | 48 | 19 | 68 |

TABLE 14

Effect of DFMA and DFMO on infection by bean powdery mildew (*Erysiphe polygoni*)

| Treatment | Percent control |
| --- | --- |
| Control | — |
| 1 mM DFMO | 35 |
| 5 mM DFMO | 45 |
| 10 mM DFMO | 52 |
| 1 mM DFMA | 7 |
| 5 mM DFMA | 35 |
| 10 mM DFMA | 35 |
| 1 mM DFMO + DFMA | 21 |
| 5 mM DFMO + DFMA | 31 |
| 10 mM DFMO + DFMA | 41 |

TABLE 15

Effect of DFMO on radial growth in vitro on cucumber anthracnose fungus (*Collectotrichum lagenarium*).

| Concentration (mM) | Radial growth (cm) | Percent control |
| --- | --- | --- |
| 0.00 | 4.5 | — |
| 0.10 | 4.5 | — |
| 0.25 | 4.5 | — |
| 0.50 | 4.5 | — |
| 0.65 | 4.4 | 2 |
| 1.00 | 4.0 | 7 |
| 5.00 | 3.8 | 16 |

TABLE 16

Effect of DFMO and DFMA on infection by cucumber anthracnose (*Colletotrichum lagenarium*).

| Concentration (mM) | Lesions per plant | Percent control |
| --- | --- | --- |
| 0.0 | 81 | — |
| 1.0 DFMO | 69 | 14 |
| 5.0 DFMO | 69 | 14 |
| 10.0 DFMO | 70 | 14 |
| 0.0 | 81 | — |
| 1.0 DFMA | 73 | 10 |
| 5.0 DFMA | 71 | 12 |
| 10.0 DFMA | 73 | 10 |
| 0.0 | 81 | — |
| 1.0 DFMO/DFMA | 73 | 10 |
| 5.0 DFMO/DFMA | 73 | 10 |
| 10.0 DFMO/DFMA | 71 | 12 |

We claim:

1. The method of protecting plants against infection by fungi by applying a fungicidally effective amount of DL-alpha-Difluoromethylornithine to the plants.

2. The method of claim 1 where pinto bean plants are given protection from infection by uredospores of the bean rust fungus.

3. The method of claim 1 where tomato plants are given protection from infection by Verticillium wilt, a fungus disease of tomato.

4. The method of claim 1 where wheat is given protection from infection by Leaf Rust fungus.

5. The method of claim 1 where wheat is given protection from infection by Stem Rust fungus.

6. The method of claim 1 where wheat is given protection from infection by Powdery Mildew fungus.

7. The method of claim 1 where Tendergreen bean plants are given protection from infection by Powdery Mildew fungus.

8. The method of claim 1 where MacIntosh apple leaves are given protection from infection by Powdery Mildew fungus.

9. The method of claim 1 where Ogle oats are given protection from infection by stem rust fungus.

10. The method of claim 1 where corn plants are given protection from infection by Corn Rust fungus.

11. The method of claim 1 where the DL-alpha-Difluoromethylornithine being sprayed onto the plants is in solution in 0.01% wetting agent dilutions as low as 0.01 mM and has given protection for the plants measured at 50% or more against the wheat leaf rust disease of plants.

12. The method of claim 1 where the DL-alpha-Difluoromethylornithine is sprayed at dilutions of 1.0 mM in a 0.01% wetting agent onto the plants up to three days after the plants have been infected by a rust fungus and complete protection against a rust fungus is obtained.

13. The method of claim 1 where the DL-alpha-Difluoromethylornithine may be applied to a portion of each of the plants to be protected and the remaining parts of each plant, including new leaves thereof, are also protected.

14. The method of claim 1 where the DL-alpha-Difluoromethylornithine may be applied to the plants, or parts thereof, and each plant, including new leaves thereof, will be protected for a period of time determined by the concentration of the DL-alpha-Difluoromethylornithine in the wetting agent.

15. The method of protecting plants against infection by obligate or non obligate parasitic fungi organisms by applying a fungicidally effective amount of DL-alpha-Difluoromethylornithine to the plants.

16. The method of protecting plants against infection by obligate parasitic fungi organisms by applying a fungicidally effective amount of DL-alpha-Difluoromethylornithine to the plants.

17. The method of protecting plants against infection by non obligate parasitic fungi organisms by applying a fungicidally effective amount of DL-alpha-Difluoromethylornithine to the plants.

18. The method of protecting a plant from fungi by spraying said plants with a fungicidally effective amount of DL-alpha-Difluoromethylornithine dissolved in a wetting agent.

* * * * *

UNITED STATES PATENT AND TRADEMARK OFFICE
CERTIFICATE OF CORRECTION

PATENT NO. : 4,818,770
DATED : April 4, 1989
INVENTOR(S) : Weinstein, et al

It is certified that error appears in the above-identified patent and that said Letters Patent is hereby corrected as shown below:

Column 1, line 5 (before Background of the Invention

This invention was made with Government support under grant number 2 R01 AG02742-03 awarded by the National Institutes of Health of the Department of Health and Human Services. The Government has certain rights in the invention.

Signed and Sealed this

Twenty-sixth Day of February, 1991

Attest:

HARRY F. MANBECK, JR.

*Attesting Officer*    *Commissioner of Patents and Trademarks*